(12) United States Patent
Abele et al.

(10) Patent No.: US 9,149,043 B2
(45) Date of Patent: Oct. 6, 2015

(54) COMPOSITIONS AND METHOD FOR PREVENTING AND TREATING FIRE BLIGHT

(76) Inventors: Ulf Abele, Hohenwart (DE); Hans Siebenlist, Schweitenkirchen (DE)

( * ) Notice: Subject to any disclaimer, the term of this patent is extended or adjusted under 35 U.S.C. 154(b) by 0 days.

(21) Appl. No.: 13/382,802

(22) PCT Filed: Jul. 9, 2010

(86) PCT No.: PCT/EP2010/004193
§ 371 (c)(1),
(2), (4) Date: Jan. 6, 2012

(87) PCT Pub. No.: WO2011/003620
PCT Pub. Date: Jan. 13, 2011

(65) Prior Publication Data
US 2012/0107422 A1 May 3, 2012

(30) Foreign Application Priority Data
Jul. 10, 2009 (DE) .......................... 10 2009 032 895

(51) Int. Cl.
*A01N 59/06* (2006.01)
*A01P 1/00* (2006.01)
*A01P 15/00* (2006.01)
*A01N 63/00* (2006.01)

(52) U.S. Cl.
CPC ...................................... *A01N 59/06* (2013.01)

(58) Field of Classification Search
CPC ... A01N 2300/00; A01N 65/00; A01N 59/00; A01N 59/16; A01N 59/06; A01N 59/02
USPC ......................................... 424/682, 405, 617
See application file for complete search history.

(56) References Cited

U.S. PATENT DOCUMENTS

| | | | | |
|---|---|---|---|---|
| 3,983,214 A | * | 9/1976 | Misato et al. | 514/53 |
| 4,053,612 A | * | 10/1977 | Baude et al. | 514/528 |
| 4,108,979 A | * | 8/1978 | Muhler et al. | 424/49 |
| 6,228,150 B1 | * | 5/2001 | Armstrong et al. | 95/139 |
| 6,352,960 B1 | * | 3/2002 | Teraoka et al. | 504/343 |
| 6,929,759 B2 | | 8/2005 | Fruh et al. | |
| 2002/0058591 A1 | * | 5/2002 | Bickers et al. | 504/211 |
| 2006/0211575 A1 | * | 9/2006 | Sedun et al. | 504/100 |
| 2011/0081507 A1 | * | 4/2011 | Zeelie et al. | 428/17 |
| 2011/0319435 A1 | * | 12/2011 | Saalfeld et al. | 514/266.23 |

FOREIGN PATENT DOCUMENTS

| | | |
|---|---|---|
| DE | 10 35 395 B | 7/1958 |
| DE | 36 29 385 A1 | 3/1987 |
| WO | WO 9727837 A1 * | 8/1997 |
| WO | WO 03007712 A1 * | 1/2003 |

OTHER PUBLICATIONS

Prankerd, Richard. Humectants and Preservatives. 2004. Slide 3.*
Dermatologists. Fungal infections. p. 1.*
Unknown Author, Aluminiumsulfat from Wikipedia, URL: http://de.wikipedia.org/wiki/Aluminiumsulfat (Nov. 23, 2012) English translation attached.
Julius Kühn Institute, Pflanzenstärkungsmittel Myco-Sin URL: http://pflanzenstaerkungsmittel.jki.bund.de/erg3.6.php?auswahl=MYS (Nov. 26, 2012) English translation attached.
BioFa, Biofa Bio-Farming-Systems: Myco-Sin URL: http://www.biofa-profi.de/de/produkte/details/myco-sin,100,2.php (Nov. 26, 2012) English Translation attached.

* cited by examiner

*Primary Examiner* — Frederick Krass
*Assistant Examiner* — Tracy Liu
(74) *Attorney, Agent, or Firm* — Timothy M. Brown, Esq.

(57) ABSTRACT

The disclosure relates to compositions for treating and/or preventing fire blight in plants or parts thereof, to their methods of production, to concentrates for producing said compositions and to uses and methods based on said compositions.

19 Claims, 1 Drawing Sheet

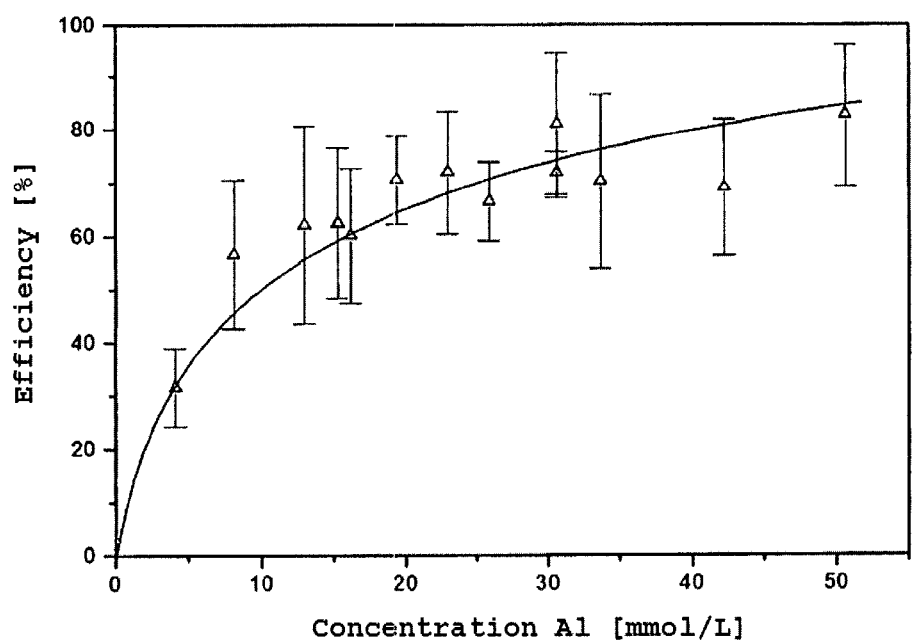

COMPOSITIONS AND METHOD FOR PREVENTING AND TREATING FIRE BLIGHT

CROSS REFERENCE TO RELATED APPLICATIONS

This application is a national phase application of PCT/EP2010/004193 filed Jul. 9, 2010 which also claims the benefit of German Application No. 10 2009 032 895.5 filed Jul. 10, 2009. The contents of the prior application are incorporated herein by reference.

TECHNICAL FIELD

The disclosure relates to compositions for treating and/or preventing fire blight in plants or parts thereof, to their methods of production, to concentrates for producing said compositions and to uses and methods based on said compositions.

BACKGROUND

Fire blight is a plant disease caused by the bacterium *Erwinia amylovora*, and is the cause of massive commercial damage worldwide, especially in the field of pomiculture. The disease is spreads rapidly and is difficult to treat and control with current agents.

Known signs for the manifestation of the disease are the dark-brown to black leaf stalks of leaves and blossoms already dead located in the proximity of diseased branches as well as the blackened midrips of the leaves. During spring and summer, sticky, moist droplets appear on the affected sprouts, fruits and on the downside of the leaves, these droplets being colorless at first but later on assume a brownish color. The infectious oozes (the bacterial exudates) preferably form under hot and humid conditions.

Traditionally, for treating fire blight already present, affected parts of the plant are removed and burned or plant protection agents containing antibiotics, e.g. streptomycin, are employed comprehensively. While burning is only marginally successful and the recurrence of disease can be prevented only if all affected plant material is completely deposited, the treatment with antibiotics is problematic for a variety of reasons. From a food technology perspective, the use of antibiotics in orchards requires elaborate testing for residual antibiotics in the treated plants as well as in the fruits produced by these trees, to ensure, in the interest of the consumer, that the fruit itself is free from antibiotics. Moreover, the development of antibiotic resistances in bacterial strains is a risk, occurring e.g. when antibiotics are applied inexpertly for extended periods of time at too low concentrations.

Furthermore, the use of plant protecting products containing antibiotics in orchards localized in the vicinity of a honey producing apicultural facility is problematic as well. Antibiotics may be taken up by worker bees and appear as undesired antibiotic residues in the honey produced by those bees.

From the state of the art, some agents suitable for treating and preventing fire blight are known which are free from antibiotics and work more or less effective. The prior art documents WO 2005/1048717, CA 2291984 and U.S. Pat. No. 4,569,841 disclose biotechnological or fermentation-based methods for treating fire blight. Finally, the documents WO 2002/1052942 and EP 0 565 266 disclose compositions containing inorganic substances for treating fire blight.

WO 2005/099454 relates to combinations of active substances which contain a valinamide derivative, a phosphonate and folpet and which can be used for combating phytopathogenic fungi and bacteria. Compositions used in the examples contain fosetyl-Al (Aliette) as an active ingredient, in which aluminum is bound to an ethylphosphonate residue. The concentration of the fosetyl-aluminum in these compositions, however, amounts to a maximum of only 250 mg/L (see Table 1 of this disclosure), which corresponds to an aluminum concentration of about 0.7 mmol/L. The principle of action of Fosetyl-Al is based on a systemic transformation into phosphonic acid and on an enhancement of the plant's resistance against harmful fungal and bacterial organisms. Additionally, in the prior art document WO 2005/099454, no pH value of the compositions is given.

Furthermore, the documents DD-A 273 192, JP-A 630099005 and GB-A 1315430 disclose methods of treatment and prevention by using known antibiotics. The documents GB 1049116, JP 1090102, U.S. Pat. No. 5,686,389, EP 1 075 185, EP 0 158 074, EP 1 300 078 and DE 3640048 disclose other organic compounds effective against fire blight.

None of the cited prior art documents, however, discloses a composition characterized by an excellent efficiency with respect to treating and preventing fire blight, while at the same time being ecologically safe and non-harmful from a health point of view in the context of food production. Moreover, none of the documents discloses a composition which contains aluminum (III) ions at the concentrations and at the specific pH value as defined in the patent claims.

OBJECT AND SHORT DESCRIPTION OF THE DISCLOSURE

It is therefore the object of the present disclosure to provide for compositions, as well as for means and methods for the production thereof, which can be used for treating and/or preventing fire blight diseases in fruit trees and/or ornamental plants, and which overcome the disadvantages of the plant protection agents of the prior art.

The object of the present disclosure is achieved by the compositions, the methods of manufacture, the concentrates for the production of the compositions, as well as the uses and methods, based on the compositions, as defined in the patent claims.

The inventors of the present disclosure have found out surprisingly, that by using the compositions thus defined, the infestation of plants or parts thereof with pests can be combated or prevented with high efficiency, especially an infestation with the bacterium *Erwinia amylovara* (fire blight disease), without affecting significantly the growth, the fruitification or the metabolism of the plants, especially of the fruit trees. The composition contains neither any organic compounds harmful to the environment nor poorly degradable pesticides and thus is characterized by a high biocompatibility.

Surprisingly, it is also possible to atomize on a large scale the compositions according to the disclosure without health hazard to humans, and to apply said compositions onto plants or parts thereof, respectively, whereby wearing a surgical or a face mask is unnecessary. In other words, the compositions are particularly mild and environmentally compatible plant protection agents, whose use in orchards will comply to a high degree with occupational safety regulations.

DETAILED DESCRIPTION

In a first aspect, the present disclosure relates to a composition containing aluminum (III) ions in an aqueous solution at a concentration of from 5 to 60 mmol/L. The pH of the composition is within the range of from 3.0 to 5.0, and the composition is particularly suited for treating and/or preventing fire blight.

It has been found out surprisingly, that a composition with features thus defined can efficiently prevent an infestation of plants or parts thereof with pests, e.g. with the bacterium *Erwinia amylovara* or that said composition also can efficiently treat an infestation which is already present. In other words, the composition according to the disclosure can be utilized as a plant protection agent.

Moreover, the inventors of the present disclosure found out surprisingly, that the composition is effective in treating a fire blight disease in or on fruit trees if the concentration of aluminum (III) ions is at least 5 mmol/L. On the other hand, it has been found that no negative effects with respect to plants and/or their respective parts are observed, if the concentration of aluminum (III) ions is not higher than 60 mmol/L. Preferably, the concentration of aluminum (III) ions is between 15 to 40 mmol/L, in particular between 25 to 40 mmol/L, as within these ranges, negative effects with respect to plants and/or their respective parts, are minimal, while at the same time, efficiency against the bacterium *Erwinia amylovara* is excellent.

The preferred counterions contained in the composition are sulfate ions. In this case, the concentration of sulfate ions is between 7.5 to 120 mmol/L, preferably between 30 to 80 mmol/L, in particular between 50 to 70 mmol/L. Using sulfate ions has the advantage that aluminum as a poorly soluble salt cannot precipitate in an aqueous solution.

For adjusting the pH within the range of from 3.0 to 5.0, it is preferred that the composition also contains further cations, preferably potassium or sodium ions at a concentration of from 5 to 60 mmol/L, preferably at a concentration of from 15 to 40 mmol/L, in particular at a concentration of from 25 to 40 mmol/L. If a composition contains potassium or sodium ions at these concentrations, the pH value of the aqueous solution can be adjusted easily to the preferred range. Sodium and potassium ions are considered non-hazardous with respect to biocompatibility and in view of occupational safety regulations.

In a preferred implementation the composition additionally contains a humectant. Any agent may be used as a humectant, which can humidify the composition after its application to plants or parts thereof over a prolonged period of time of several days to weeks, as for example glycerin, propylene glycol, polyethylene glycol, sodium lactate, potassium lactate, calcium lactate, sorbitol, xylitol, glycerol, maltitol, invertase, polydextrose, magnesium chloride hexahydrate, ammonium chloride and their hydrates, calcium chloride and their hydrates, calcium nitrate and their hydrates or mixtures of two or more of these substances. In general, the humectant is a hygroscopic salt or a hygroscopic organic compound. Preferably, the composition contains magnesium chloride hexahydrate as a humectant at a concentration of from 2 to 40 mmol/L. More preferably, the concentration of the humectant is from 10 to 35 mmol/L, and in particular, the concentration of the humectant is from 20 to 30 mmol/L. Ideally, the humectant does not form any poorly soluble salts with the aluminum (III) ions also present in the composition, such that all active ingredients of the composition remain in solution even when the composition is stored for an extended period of time or when exposed to heat and/or cold temperatures.

Due to the humectant, the composition can act on the bacterial pests for an extended period of time after being applied to the plants or the parts thereof, such that altogether, efficiency is higher and more prolonged.

It is preferred that the composition contains, in addition, a spreading agent at a concentration in the range of from 0.0025 to 2 g/L, preferably at a concentration in the range of from 0.01 to 1 g/L, in particular at a concentration of 0.5 g/L.

Spreading agents are agents, which are able to enhance the spreading of the composition on the plants or their respective parts. Examples of spreading agents, which may be contained in the composition are silicone oils of various degrees of viscosity, fatty acid esters such as ethyl stearate, lauric acid hexyl ester, dipropylene glycol pelargonate, esters of branched fatty acids of a medium chain length with saturated fatty alcohols $C_{16}$-$C_{18}$, such as isopropyl myristate, isopropyl palmitate, caprylic/capric acid esters of saturated fatty alcohols of a chain length $C_{16}$-$C_{18}$, isopropyl stearate, decyl oleate esters, oleyl oleate esters, waxy fatty acid esters, diisopropyl adipate ester, caprylic/capric acid triglyceride, triglyceride mixtures with vegetable fatty acids of chain length $C_8$-$C_{12}$ or other specifically selected natural fatty acids, partial glyceride mixtures of saturated or unsaturated, optionally hydroxyl-containing fatty acids, monoglycerides of the $C_8$-$C_{10}$-fatty acids, isopropyl myristate, isopropyl stearate, isopropyl palmitate, lauric acid hexyl esters, decyl oleate esters, dibutyl stearate, dibutyl sebacate, paraffin oil, ethylhexyl palmitate/stearate, ethylhexyl palmitate/isotridecyl stearate, mixtures of isopropyl myristate, isopropyl palmitate, isopropyl stearate and combinations thereof.

Preferably the spreading agent is a non-ionic, cationic or amphoteric surfactant. For example, the surfactant may be an anionic surfactant selected from the group consisting of alkyl sulfate, alkyl ether sulfate, alkylaryl sulfonate, alkyl succinate, alkyl sulfosuccinate, N-acyloyl sarcosinate, acyl taurate, alkyl isethionate, alkyl phosphate, alkyl ether phosphate, alkyl ether carboxylate, alpha olefin sulfonate, in particular alkali metal salts and alkaline earth metal salts, e.g. sodium, potassium, magnesium, calcium, ammonium and triethanolamine salts. The alkyl ether sulfates, alkyl ether phosphates and alkyl ether carboxylates may e.g. comprise between 1 and 10 units of ethylene oxide or propylene oxide, respectively, preferably 1 to 3 units of ethylene oxide. Suitable compounds are e.g. sodium lauryl sulfate, ammonium lauryl sulfate, sodium lauryl ether sulfate, ammonium lauryl ether sulfate, sodium lauroyl sarcosinate, sodium oleoyl succinate, ammonium lauryl sulfosuccinate, sodium dodecylbenzenesulfonate, triethanolamine dodecylbenzenesulfonate.

Preferably, the spreading agent is a non-ionic surfactant, however. Examples for non-ionic surfactants, which may be present in the composition according to the disclosure, comprise esters of sucrose, especially mono-, di- and triesters of sucrose with fatty acids, lecithins, in particular with phosphatidylcholines, phosphatidylethanolamines and phosphatidylinositoles, polyethylene glycol ethers, fatty alcohol ethoxylates, fatty alcohol propoxylate, alkyl glycosides, alykl polyglucosides, octylphenol ethoxylate and nonylphenol ethoxylate and combinations thereof. In an especially preferred implementation, the spreading agent is a polyethoxylated castor oil. A particularly preferred polyethoxylated castor oil is the commercially available Cremphor EL. Particularly preferred spreading agents are esters of sucrose due to their excellent biocompatibility and environmental safety characteristics, especially mono-, di- and triesters of sucrose with fatty acids, and lecithins, in particular phosphatidylcholines, phosphatidylethanolamines and phosphatidylinositols.

Compositions containing spreading agents adhere especially well to plants and parts thereof, and thereby enhance the efficiency of the compositions. Preferably, the spreading agent exhibits good water solubility.

In a preferred embodiment, the composition contains aluminum (III) ions at a concentration of from 5 to 60 mmol/L, a humectant at a concentration of from 2 to 40 mmol/L, and a spreading agent at a concentration of from 0.0025 to 2 g/L in an aqueous solution at a pH within the range of from 3.0 to 5.0, preferably at a pH within the range of from 3.3 to 4.0.

It was observed that compositions with a pH as defined above remain stable even when stored for an extended period of time of several weeks to months, and that aluminum(III) ions do not precipitate from these compositions as salts during storage. At the same time, the compositions provide for a high efficiency when treating fire blight in or on fruit trees.

The compositions may comprise, in addition, one or more wetting agents, as for example alkali metal salts, alkaline earth metal salts and ammonium salts of aromatic sulfonic acids, e.g. [ligno-, phenol-, naphthalene- and dibutylnaphthalenesulfonic acids, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ether or polyoxypropylene alkyl ether, lauryl alcohol polyglycol ether acetate, sorbitol ester, lignosulfite waste liquors or methyl cellulose. With respect to the concentration of the wetting agent, if present, the compositions may contain said wetting agents at a concentration of 0.01 to 8% by weight, preferably at a concentration of 0.2 to 6% by weight, especially at a concentration of 0.3 to 5% by weight, and in particular at a concentration of 0.5 to 3% by weight.

The composition may contain, in addition, one or more emulsifiers, as for example sodium salts, potassium salts and ammonium salts of straight-chain aliphatic carboxylic acids of a chain length $C_{12}$-$C_{20}$, sodium hydroxyoctadecanesulfonate, sodium salts, potassium salts and ammonium salts of hydroxy fatty acids of a chain length $C_{12}$-$C_{20}$ and their sulfation or acetylation products, alkyl sulfates, also as triethanolamine salts, ($C_{10}$-$C_{20}$)-alkylsulfonates, ($C_{10}$-$C_{20}$)-alkylarylsulfonates, dimethyl-di($C_8$-$C_{18}$)-alkylammonium chloride, acyl-, alkyl-, oleyl- and alkylaryloxethylates and their sulfation products, alkali metal salts of esters of sulfosuccinic acid with aliphatic saturated monohydric alcohols of a chain length $C_4$-$C_{16}$, sulfosuccinic acid 4-esters with polyethylene glycol ethers of monohydric aliphatic alcohols of a chain length $C_{10}$-$C_{12}$ (disodium salt), sulfosuccinic acid 4-esters with polyethylene glycol nonylphenyl ether (disodium salt), biscyclohexyl sulfosuccinic acid ester (sodium salt), lignosulfonic acid and its calcium, magnesium, sodium and ammonium salts, polyoxyethylene sorbitan monooleate with 20 ethylene oxide groups, resin acids, hydrogenated and dehydrogenated resin acids and their alkali metal salts, dodecylated sodium diphenyl ether disulfonate, and copolymers of ethylene oxide and propylene oxide with a minimum content of 10% by weight of ethylene oxide. Preferred emulsifiers are sodium lauryl sulfate, sodium lauryl ether sulfate, ethoxylated (3 ethylene oxide groups), polyethylene glycol(4-20) ethers of oleyl alcohol and polyethylene oxide(4-14) ethers of nonylphenol. With respect to the concentration of the emulsifiers, if present, the compositions may contain said emulsifiers at a concentration of from 0.01 to 15% by weight, preferably at a concentration of from 0.2 to 8% by weight, especially at a concentration of from 0.5 to 6% by weight, and in particular at a concentration of from 1 to 5% by weight.

The composition may contain, in addition, one or more dispersing agents, such as alkylphenol polyglycol ether. With respect to the concentration of the dispersing agents, if present, the compositions may contain said dispersing agents e.g. at a concentration of from 0.01 to 8% by weight, preferably at a concentration of from 0.1 to 6% by weight, especially at a concentration of from 0.2 to 5% by weight, and in particular at a concentration of from 0.4 to 3% by weight.

The composition may contain, in addition, one or more stabilizing agents, such as cellulose or its derivatives. With respect to the concentration of the stabilizing agents, if present, the compositions may contain said stabilizing agents at a concentration of 0.01 to 6% by weight, preferably at a concentration of from 0.01 to 3% by weight, especially at a concentration of from 0.01 to 2% by weight, and in particular at a concentration of from 0.01 to 1% by weight.

The composition may contain, in addition, one or more adhesives, such as carboxymethyl cellulose, natural and synthetic polymers in the form of powders, granules or latices, such as gum arabic, polyvinyl alcohol and polyvinyl acetate, natural phospholipids, such as cephalins and lecithins, and synthetic phospholipids, as well as paraffin oils. With respect to the concentration of the adhesives, if present, the compositions may contain said adhesives at a concentration of from 0.01 to 8% by weight, preferably at a concentration of from 0.1 to 4% by weight, especially at a concentration of from 0.2 to 3% by weight, and in particular at a concentration of from 0.2 to 2% by weight.

The composition may contain, in addition, one or more organic solvents, such as mono- or polyhydric alcohols, esters, ketones and hydrocarbons, such as paraffins, petroleum fractions, mineral and vegetable oils, butanol or glycol and their ethers and esters, ketones, such as acetone, methyl ethyl ketone, methyl isobutyl ketone, or cyclohexanone. With respect to the concentration of the organic solvents, if present, the compositions may contain said organic solvents at a concentration of from 0.01 to 25% by weight, preferably at a concentration of from 0.2 to 12% by weight, especially at a concentration of from 0.5 to 7% by weight, and in particular at a concentration of from 1 to 4% by weight.

The composition may contain, in addition, one or more scents or dyestuffs, as for example inorganic pigments, such as iron oxide, titanium oxide, Prussian blue, organic dyestuffs, such as alizarin dyestuffs, azo dyestuffs and metal phthalocyanine dyestuffs and mineral nutrients, such as salts of iron, manganese, boron, copper, cobalt, molybdenum and zinc. With respect to the concentration of the scents or dyestuffs, if present, the compositions may contain said scents or dyestuffs at a concentration of from 0.001 to 4% by weight, preferably at a concentration of from 0.01 to 1% by weight, especially at a concentration of from 0.01 to 0.8% by weight.

The composition may contain, in addition, one or more dedusting agents, as for example polyglycols or polyglycol ethers. With respect to the concentration of the dedusting agents, if present, the compositions may contain said dedusting agents at a concentration of from 0.01 to 2% by weight, preferably at a concentration of from 0.05 to 1% by weight, especially at a concentration of from 0.1 to 0.5% by weight.

The composition may contain, in addition, one or more buffering substances, buffer systems or pH regulators. With respect to the concentration of the buffering substances, buffer systems or regulators of pH, if present, the compositions may contain said buffering substances, buffer systems or regulators of pH at a concentration of from 0.01 to 10% by weight, preferably at a concentration of from 0.1 to 5% by weight.

The composition may contain, in addition, further active ingredients alone or in combinations thereof, such as bactericides, fungicides, insecticides, acaricides and growth regulators. Preferably, the concentration of further active ingredients contained in the compositions does not exceed a maximum concentration of 10% by weight, preferably does not exceed a maximum concentration of 2% by weight, in particular, no further active ingredients are contained in the compositions.

In a preferred implementation, the composition is free of phosphorus containing compounds. In particular, the compositions according to the disclosure do not comprise a phosphorus containing compound, which may be transformed into phosphonic acid or its derivatives by the plant's metabolic pathways.

It was surprisingly found out, that with compositions thus defined plants or parts thereof could also be protected against or treated with respect to an infestation with fungi from the Oomycetes group, without detecting phosphonic acid containing residues in plants or their respective parts despite a seasonally late application starting in July. Moreover, the compositions do not release compounds containing phosphonic acid, which are potentially hazardous to water. According to German regulations, phosphonic acid is classified as belonging to water hazard class 1 (Wassergefährungsklasse, WGK 1), i.e. it is considered mildly hazardous to water.

In a preferred implementation, the composition is a plant protecting agent or a pesticide. In other words, the composition can be used for protection or treatment of a plant or a part thereof with respect to infestation with phytopathogenic fungi, bacteria and/or viruses.

The present disclosure also relates to a concentrate suitable for producing the composition. The concentrate contains an aluminum salt, a spreading agent and a humectant. Preferably, the concentrate exhibits good solubility in water. In this way, the concentrate can be easily transformed into the composition of the disclosure.

The concentrate allows for efficient storage of the plant protecting agent, which can be dissolved easily in water on-site and thus be transformed into a preparation suitable for application to plants or parts thereof. Ideally, the concentrate may be stored for longer periods of time, i.e. for several weeks or months, without structural changes. By way of its formulation as concentrate, costs of storage as well as of transportation can be reduced significantly in comparison to a ready-to-use aqueous composition. Advantageously, the concentrate is also non-hazardous at skin contact.

The concentrate can be formulated e.g. as a solid concentrate, for example in the form of powder, pellets, granulate, capsules or tablets, or as a semisolid or fluid concentrate, such as a gel, a liquid concentrate or a suspension, if desired, the concentrate can be formulated and packaged in portions. Especially with respect to good storage and transport characteristics, a granular concentrate is preferred, in particular a dust-free microgranulate, which can be dissolved easily in water.

In a preferred implementation, the composition contains potassium aluminum sulfate dodecahydrate, magnesium sulfate hexahydrate, and a spreading agent. Particularly preferred is a concentrate containing potassium aluminum sulfate dodecahydrate at a concentration of from 50 to 80% by weight, magnesium sulfate hexahydrate at a concentration of from 10 to 40% by weight, and a spreading agent at a concentration of from 0.1 to 10% by weight.

By dissolving in water, such a concentrate can be transformed easily into the composition of the disclosure, suited for application to plants or parts thereof, without the necessity of adjusting the pH.

In a further aspect, the disclosure relates to a method for manufacturing the composition of the disclosure. The method of manufacture thereby comprises at first a step of diluting with water a concentrate according to the disclosure, preferably conducted while stirring. Optionally, the method of manufacture may comprise a further step of adjusting the pH to a value within the range of from 3.0 to 5.0.

As a diluting agent, any kind of water can be used, such as tap water, rainwater, or unpurified or purified surface water, collected from water bodies or rivers. The pH adjustment in the optional second step is carried out using either a strong acid, such as concentrated sulfuric or hydrochloric acid, or a strong base, such as caustic soda solution or caustic potash solution.

The method for manufacturing the composition of the disclosure is characterized by its simplicity. In particular, the composition can be produced in a ready-to-use form also on-site, e.g. in an orchard or a plantation for ornamental plants, by adding water to the concentrate. During manufacture, all security measures normally employed for the production of other plant protection agents can be omitted substantially, as no hazardous substances or substances harmful to health are utilized. Aluminum salts are particularly suitable with respect to handling and application, as they are present ubiquitously and therefore do not harbor any appreciable risks regarding humans and/or the environment.

According to the disclosure, the composition thus manufactured may be employed in agriculture, in forestry, in gardening, in pomiculture, in vector control, in plant cultivation, in plant breeding, in generative and vegetative propagation material, in seedstock, or in non-agricultural applications for the controlling or combating of organisms.

In a further aspect the disclosure relates to a method for combating pests in plants, wherein the pests are contacted with the composition according to the disclosure. Preferably, the method can be utilized for preventing a fire blight disease in fruit trees and/or ornamental plants or for treating a fire blight disease already manifested.

As a plant any plant may be regarded, which can be infested with pests. In particular, the present disclosure comprises a method for treating fire blight in fruit trees and ornamental plants. Examples of plants which are amenable to protection by or treatment with the composition according to the disclosure are plants such as apple trees (*malus*), pear trees (*pyrus*), evergreen thorn (*pyracanth*), quince tree (*cydonia*), stranvaesia (*stranvaesia*), as well as *sorbus* trees, such as common whitebeam (*sorbus*), hawthorn and pink hawthorn (*crategus*), flowering quince (*chaenomeles*), cotoneaster (*cotoneaster*), eriobotrya (*eriobotrya*) and medlar (*mespilus*).

For prevention or treatment, the composition is applied to the plant or at least to a part of the plant in a known fashion. In this context, it is important that the fire blight causing bacterium, *Erwinia Amylovara*, is contacted with the composition, such that said composition can exert its biological effects. In a preferred implementation, the application is accomplished by spraying or brushing, most preferred by spraying, the plants with the composition according to the disclosure. The application to plants or parts thereof can be carried out for prevention purposes or, in the case of an infestation already manifested, for treatment.

In a preferred implementation, the composition is sprayed onto the plants or their respective parts in an amount of from 50 to 1,000 L/ha, preferably in an amount of from 300 to 600

L/ha, especially in an amount of 500 L/ha, whereby 1 ha corresponds to about 2.47105 acres. By employing this amount, the composition is utilized in a particularly economical and cost-effective way, while at the same time achieving excellent efficiency against fire blight.

For combating primary fire blight in pome fruit, treatment is conducted by way of one to five applications during blossoming, in particular by way of two to three applications during blossoming.

For combating secondary fire blight in pome fruit, treatment may be conducted from the beginning of the pink bud stage up to the pre-harvesting stage by way of one to ten applications, preferably by way of three to eight applications, especially by way of five to six applications.

In the following, the present disclosure will be illustrated further by individual examples and figures. These examples and figures only serve to illustrate the general inventive concept and should not be construed as limiting the disclosure in any way.

SHORT DESCRIPTION OF THE FIGURE

FIG. 1 shows the dependency of the compositions' efficiency on the concentration of aluminum (III) ions contained in the composition in the context of treating fire blight on apple tree blossoms.

EXAMPLES

Materials

All substances used are commercially available. Potassium aluminumsulfate dodecahydrate ($KAl(SO_4)_2.12(H_2O)$, Purity: "pure, crystal powder") and magnesiumchloride hexahydrate ($MgCl_2.6H_2O$, Purity: "Ph. Eur.") were obtained from Dr. Paul Lohmann GmbH KG, Emmerthal. Cremophor EL (Polyoxyethylenglyceroltriricin-oleat 35 (DAC), Polyoxyl 35 Castor Oil) is a registered trademark of BASF Corp. It was obtained from Sigma-Aldrich, Munich.

Measuring the Efficiency Against Fire Blight

For measuring the efficiency of the aqueous compositions, 24 blossoms of the apple varieties Braeburn, Jona Gold and Gala are placed in sugar solution and inoculated with a suspension of *Erwinia amylovara* at $10^6$ bacterial cells. One hour after inoculation, the blossoms are sprayed, respectively, with the composition to be tested or with water, serving as a negative control, until completely wetted. These blossoms are incubated for 6 days at 20 to 23° C. and at a relative humidity of 100%. The number of blossoms exhibiting bacterial ooze is identified.

The efficiency specifies the decrease of infested blossoms utilizing the composition to be tested in comparison to blossoms, which were treated with water only. All tests are conducted three to six times, and from the measured data the empirical mean of the efficiency, as well as the empirical standard deviation σ are calculated, whereby the standard deviation σ represents the arithmetic mean of all squared deviations of the data from the arithmetic mean of the efficiency.

Example 1

Potassium aluminum sulfate dodecahydrate, magnesium chloride hexahydrate and Cremophor EL are mixed at concentrations as indicated in table 1 to produce a concentrate of example 1.

TABLE 1 concentrate of example 1

| ingredient | net weight (wt-%) |
|---|---|
| $KAl(SO_4)_2\bullet 12(H_2O)$ | 77.0 |
| $MgCl_2\bullet 6H_20$ | 19.2 |
| Cremophor EL | 3.8 |

The concentrate of example 1 is dissolved in water at the concentrations indicated in table 2, while stirring. In the process, pH adjusts to 3.5 to 3.7. In addition, a solution of streptomycin is prepared by dissolving streptomycin to a concentration of 0.06% by weight in water. The compositions are tested with respect to their efficiency against fire blight as described above. The results are summarized in table 2.

TABLE 2 results of compositions of example 1

| | concentration (% by weight) | mean of efficiency (%) | standard deviation σ from mean |
|---|---|---|---|
| concentrate | 0.25 | 32 | 7 |
| concentrate | 0.50 | 57 | 14 |
| concentrate | 1.00 | 60 | 13 |
| streptomycin | 0.06 | 74 | 5 |

Application of compositions containing a dilution of the concentrate in the range of 0.25 to 1.00% by weight resulted in a reduction of the number of infested blossoms by up to 60 as apparent from table 2. Overall, the efficiency of the composition is almost the same as the efficiency of a commonly used solution containing 0.06% by weight of streptomycin.

Example 2

A concentrate is prepared as described in example 1, using the mass fractions as indicated in table 3.

TABLE 3 concentrate of example 2

| ingredient | mass fraction (wt-%) |
|---|---|
| $KAl(SO_4)_2\bullet 12(H_2O)$ | 72.7 |
| $MgCl_2\bullet 6H_20$ | 18.2 |
| Cremophor EL | 9.1 |

The concentrate is dissolved in water at the concentrations indicated in table 4 while stirring. In the process, pH adjusts to 3.5 to 3.7. The compositions thus prepared are tested against fire blight as described above. The results are summarized in table 4.

TABLE 4 results of compositions of example 2

| | concentration (% by weight) | mean of efficiency (%) | standard deviation σ from mean |
|---|---|---|---|
| concentrate | 1.0 | 63 | 14 |
| concentrate | 1.5 | 72 | 11 |
| concentrate | 2.00 | 81 | 14 |
| streptomycin | 0.06 | 70 | 1 |

Application of compositions containing a dilution of the concentrate of example 2 in the range of 1 to 2% by weight resulted in a reduction of the number of infested blossoms by up to 81% as apparent from table 4. Overall, the efficiency was higher when compared to a commonly used solution containing 0.06% by weight of streptomycin.

Example 3

A concentrate is prepared as described in example 1, using the mass fractions as indicated in table 5.

TABLE 5 concentrate of example 3.

| ingredient | mass fraction (wt-%) |
|---|---|
| $KAl(SO_4)_2 \cdot 12(H_2O)$ | 61.5 |
| $MgCl_2 \cdot 6H_2O$ | 30.8 |
| Cremophor EL | 7.7 |

The concentrate is dissolved in water at the concentrations indicated in table 6 while stirring. In the process, pH adjusts to 3.5 to 3.7. The compositions thus prepared are tested against fire blight as described above. The results are summarized in table 6.

TABLE 6 results of compositions of example 3

| | concentration (% by weight) | mean of efficiency (%) | standard deviation σ from mean |
|---|---|---|---|
| concentrate | 1.0 | 62 | 19 |
| concentrate | 1.5 | 71 | 8 |
| concentrate | 2.00 | 67 | 7 |
| streptomycin | 0.06 | 70 | 1 |

Application of compositions containing a dilution of the concentrate of example 3 in the range of 1.0 to 2.0% by weight resulted in a reduction of the number of infested blossoms by up to 71% as apparent from table 6. Overall, the efficiency was higher when compared to a commonly used solution containing 0.06% by weight of streptomycin.

Example 4

A concentrate is prepared as described in example 1, using the mass fractions as indicated in table 7.

TABLE 7 concentrate of example 4.

| ingredient | mass fraction (wt-%) |
|---|---|
| $KAl(SO_4)_2 \cdot 12(H_2O)$ | 72.7 |
| $MgCl_2 \cdot 6H_2O$ | 18.2 |
| Cremophor EL | 9.1 |

The concentrate is dissolved in water at the concentrations indicated in table 8 while stirring. In the process, pH adjusts to 3.5 to 3.7. The compositions thus prepared are tested against fire blight as described above. The results are summarized in table 8.

TABLE 8 results of compositions of example 4

| | concentration (% by weight) | mean of efficiency (%) | standard deviation σ from mean |
|---|---|---|---|
| concentrate | 2.0 | 72 | 4 |
| streptomycin | 0.06 | 75 | 12 |

Application of compositions containing a dilution of the concentrate at 0.25% by weight resulted in a reduction of the number of infested blossoms by up to 72% as apparent from table 8. Overall, the efficiency of the composition is almost the same as the efficiency of a commonly used solution containing 0.06% by weight of streptomycin.

Example 5

Three different concentrates A, B and C are prepared as described in example 1, using the weights as indicated in table 9.

TABLE 9 concentrates A, B and C of example 5

| | net weight (g) | | |
|---|---|---|---|
| ingredient | concentrate A | concentrate B | concentrate C |
| $KAl(SO_4)_2 \cdot 12(H_2O)$ | 16.0 | 20.0 | 24.0 |
| $MgCl_2 \cdot 6H_2O$ | 4.0 | 5.0 | 6.0 |
| Cremophor EL | 2.0 | 2.0 | 2.0 |

All concentrates A, B and C are diluted to 1.0 liter in water while stirring to obtain the respective compositions A, B and C. The pH of all compositions thus prepared is in the range of from 3.5 to 3.7 in each case. An aqueous solution of streptomycin (0.06% by weight) is used as a positive control.

The efficiency against fire blight is investigated as described above. The results are summarized in table 10.

TABLE 10 results of the concentrates of example 5

| | mean of efficiency (%) | standard deviation σ from mean |
|---|---|---|
| A | 70 | 16 |
| B | 69 | 13 |
| C | 83 | 13 |
| streptomycin | 74 | 4 |

Application of compositions A, B and C resulted in an efficiency approximating the efficiency of a commonly used solution containing 0.06% by weight of streptomycin, as apparent from table 10. Particularly efficient is composition C, leading to a reduction of the number of infested blossoms of about 83%.

The results from the examples 1 to 5 are summarized in a graphical format in FIG. 1. FIG. 1 clearly illustrates the dependency of the composition's efficiency against fire blight on the concentration of aluminum (III) ions contained in the composition, irrespective of the concentrations of the humectant and the spreading agent. In the range of from 5 to 60 mmol/L, especially in the range of from 20 to 60 mmol/L of aluminum (III) ions in the ready-to-use solution, the efficiency is in approximate correspondence to the efficiency of a commonly used solution containing 0.06% by weight of streptomycin, while the disadvantages associated with the streptomycin containing solution, however, are not observed, such as development of antibiotic resistance in microorganisms as well as accumulation of residual active substances in fruits.

The invention claimed is:

1. A composition for treating or preventing progression of fire blight, containing aluminum (III) ions as free ions in an aqueous solution at a concentration of 25 to 60 mmol/L, wherein the pH of the composition is within the range of from 3.0 to 5.0, and additionally containing a humectant, wherein said humectant is magnesium chloride hexahydrate.

2. The composition according to claim 1, wherein the magnesium chloride hexahydrate is contained in the composition at a concentration of from 2 to 40 mmol/L.

3. The composition according to claim 2, additionally containing a spreading agent at a concentration of from 0.0025 to 2 g/L.

4. The composition according to claim 3, wherein the pH of said aqueous solution is within the range of from 3.3 to 4.0.

5. The composition according to claim 4, additionally containing sulfate ions at a concentration of from 7.5 to 120 mmol/L.

6. The composition according to claim 1, additionally containing a spreading agent at a concentration of from 0.0025 to 2 g/L.

7. The composition according to claim 6, wherein the pH of said aqueous solution is within the range of from 3.3 to 4.0.

8. The composition according to claim 7, additionally containing sulfate ions at a concentration of from 7.5 to 120 mmol/L.

9. The composition according to claim 2, wherein the pH of said aqueous solution is within the range of from 3.3 to 4.0.

10. The composition according to claim 9, additionally containing sulfate ions at a concentration of from 7.5 to 120 mmol/L.

11. The composition according to claim 1, additionally containing sulfate ions at a concentration of from 7.5 to 120 mmol/L.

12. The composition according to claim 3, wherein said composition is free of phosphorus containing compounds.

13. The composition according to claim 3, wherein said composition is a pesticide.

14. A method for combating pests by applying a composition according to claim 1 to a subject in need thereof.

15. A method for preventing progression of or treating fire blight in fruit trees and ornamental plants, wherein the trees and plants are contacted with a composition according to claim 1.

16. The method according to claim 15, wherein said composition is sprayed or brushed onto the plants.

17. The method according to claim 15, wherein said composition is sprayed onto the plants in an amount of from 50 to 1,000 L/ha.

18. The composition according to claim 1, wherein the aluminum (III) ions are present at a concentration of from 25 to 40 mmol/L.

19. The composition according to claim 1, wherein the composition is free of antibiotics.

* * * * *